United States Patent [19]

Jensen

[11] 4,280,498

[45] Jul. 28, 1981

[54] VALVED DRAIN ASSEMBLY FOR UROSTOMY POUCH

[75] Inventor: Marvin E. Jensen, Niles, Ill.

[73] Assignee: Hollister Incorporated, Chicago, Ill.

[21] Appl. No.: 86,832

[22] Filed: Oct. 22, 1979

[51] Int. Cl.³ .............................................. A61F 5/44
[52] U.S. Cl. .................................. 128/283; 251/310; 251/352
[58] Field of Search ..................... 128/283, 274, 294; 251/310, 352, DIG. 5; 222/548, 555

[56] References Cited

U.S. PATENT DOCUMENTS

| | | | |
|---|---|---|---|
| 3,185,179 | 5/1965 | Harautuneian | 128/274 |
| 3,481,336 | 12/1969 | Ipson | 128/283 |
| 3,506,239 | 4/1970 | Johnson | 251/310 |
| 3,564,620 | 2/1971 | Clark | 128/295 |
| 3,822,704 | 7/1974 | Nolan | 128/283 |
| 3,974,869 | 8/1976 | Abe et al. | 251/310 |
| 4,003,403 | 1/1977 | Nehring | 251/DIG. 5 |
| 4,055,179 | 10/1977 | Manschot et al. | 128/295 |
| 4,147,184 | 4/1979 | Jess | 251/DIG. 5 |

*Primary Examiner*—Robert W. Michell
*Assistant Examiner*—J. L. Kruter
*Attorney, Agent, or Firm*—Tilton, Fallon, Lungmus

[57] ABSTRACT

A drain assembly for a urostomy pouch or other similar collection device for permitting continuous overnight draining of the pouch into a suitable receptacle, thereby allowing the user to wear the pouch in bed without the risk of fluid leakage or the inconvenience of interrupting sleep for periodic emptying of the pouch. The assembly includes a body member adapted to be secured to a pouch at the lower end thereof and defining a path for the outflow of the fluid contents of the pouch, a rotary valve member for selectively opening and closing the flow passage, and a drainage tube equipped with a coupler for releasably engaging a stem portion of the valve member.

41 Claims, 12 Drawing Figures

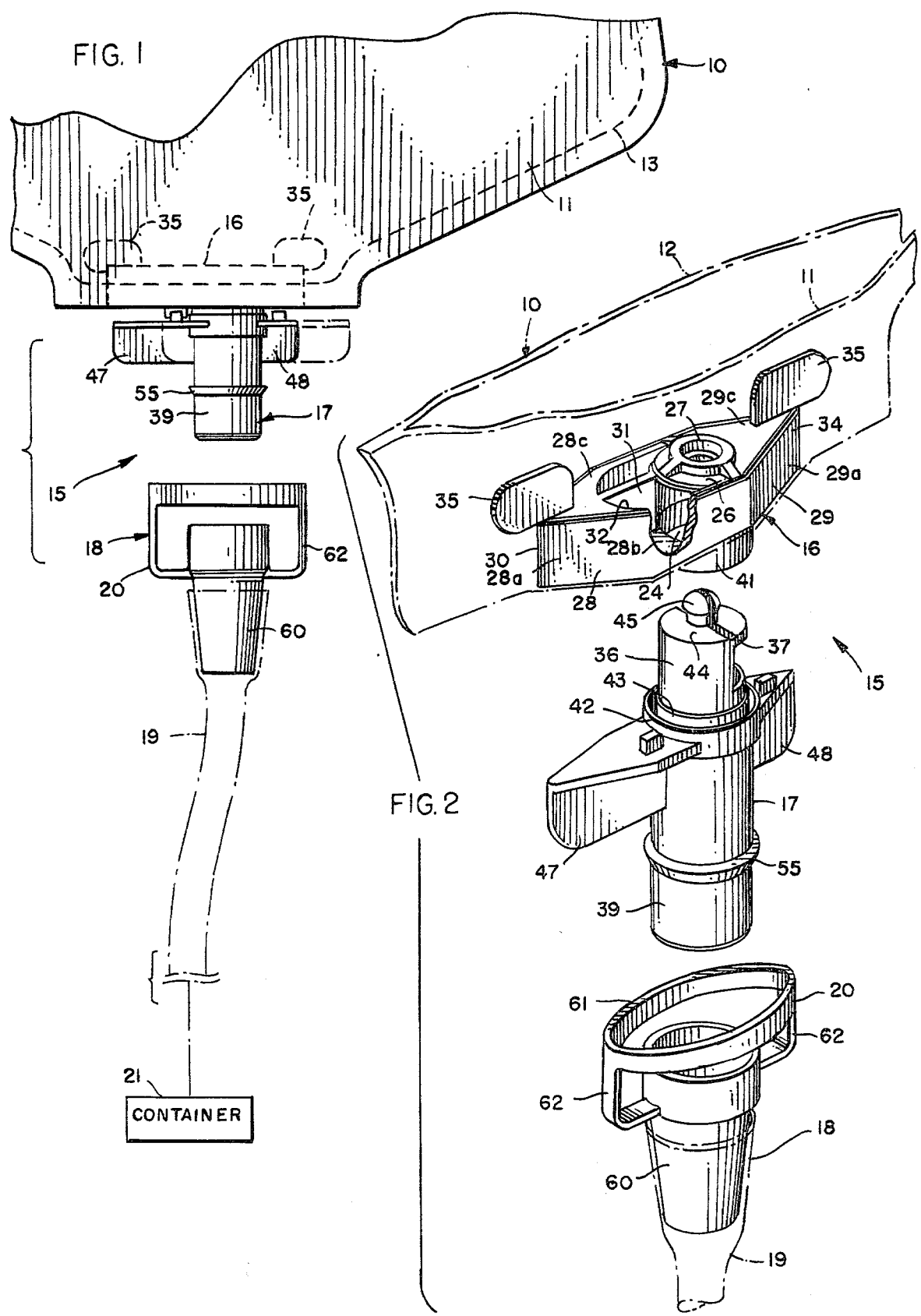

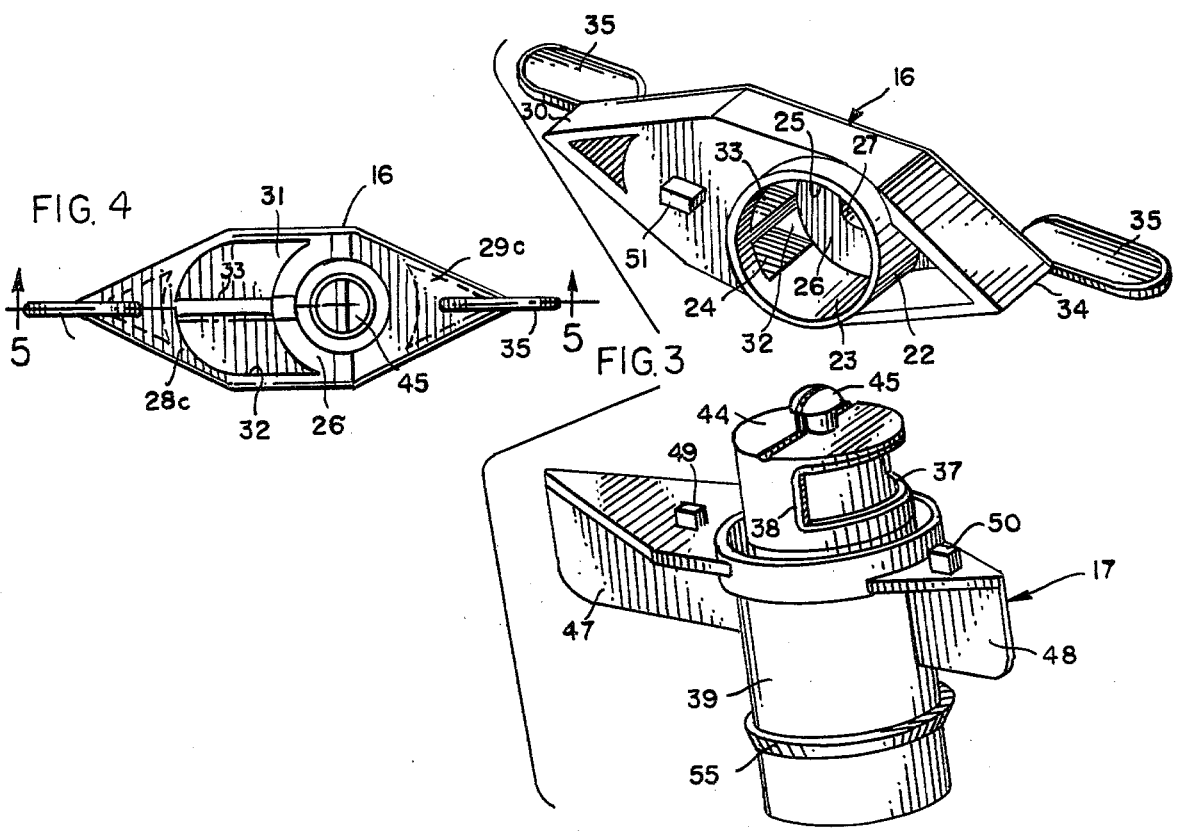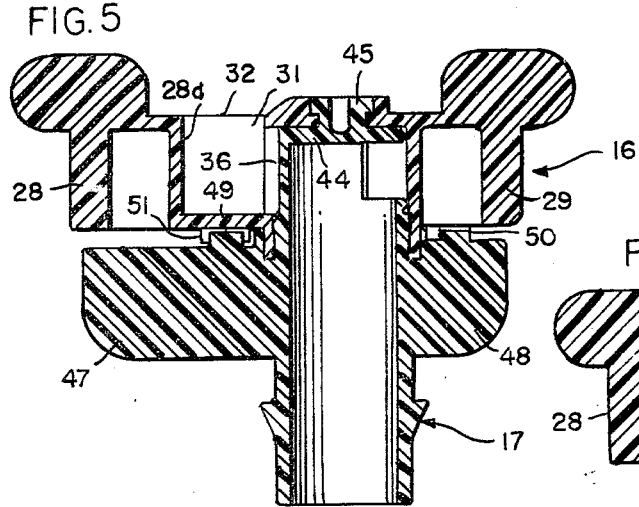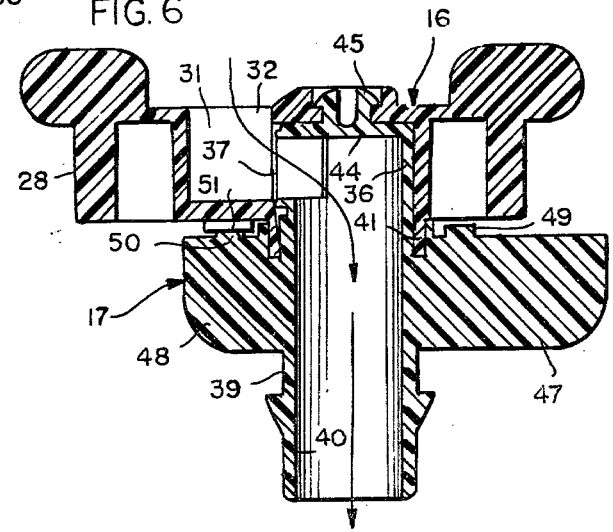

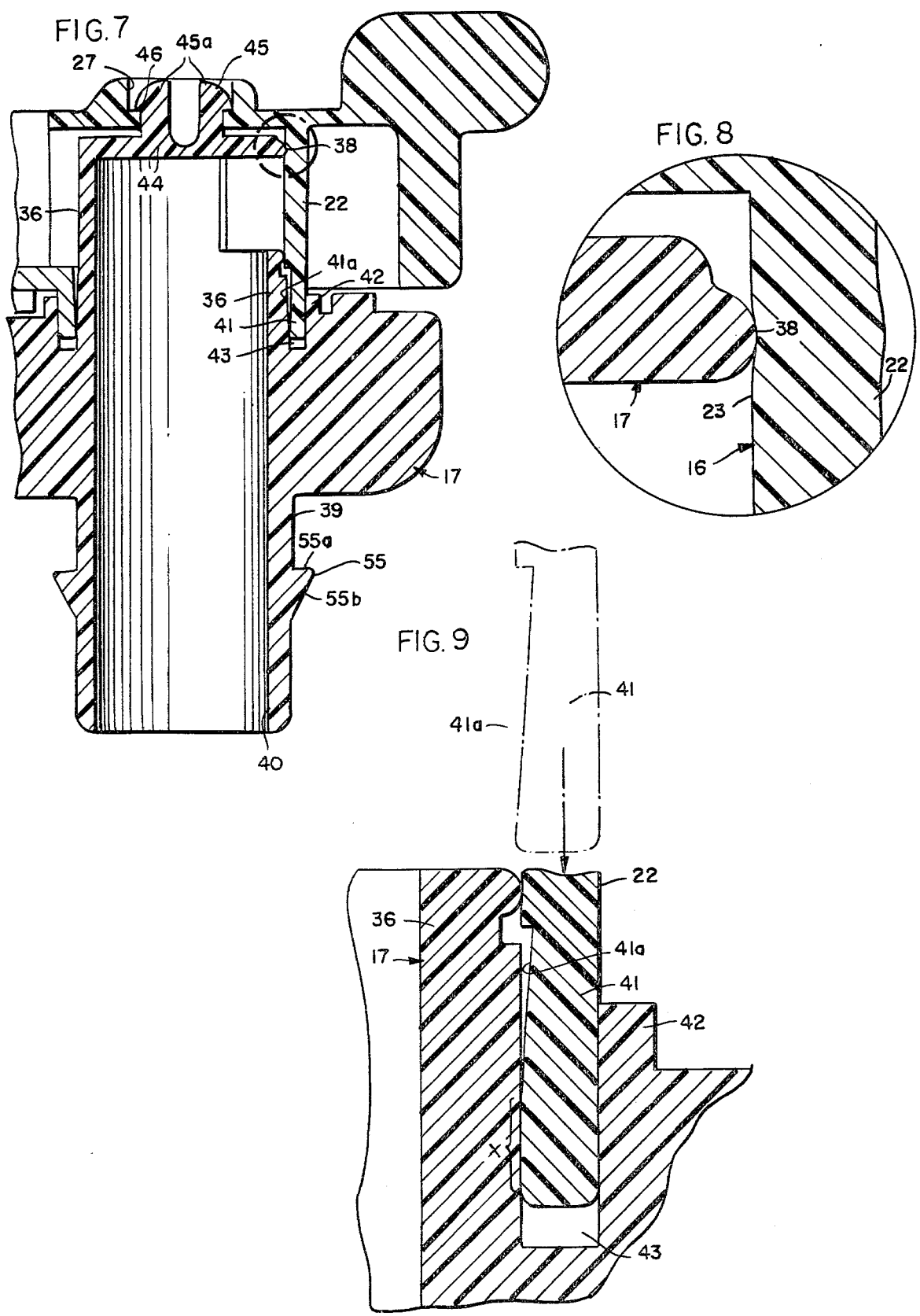

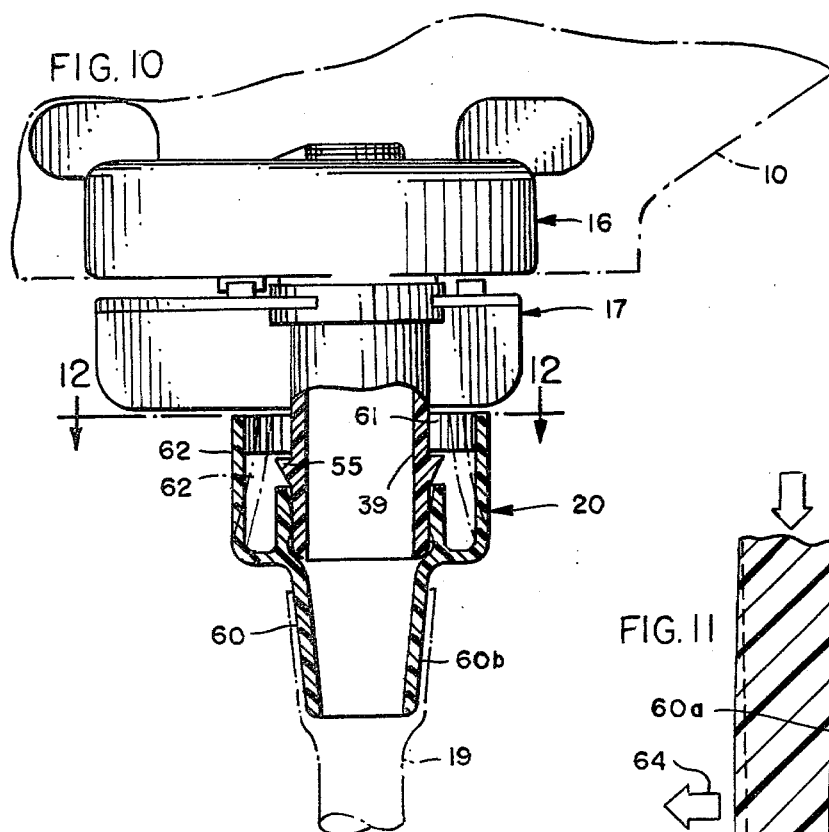
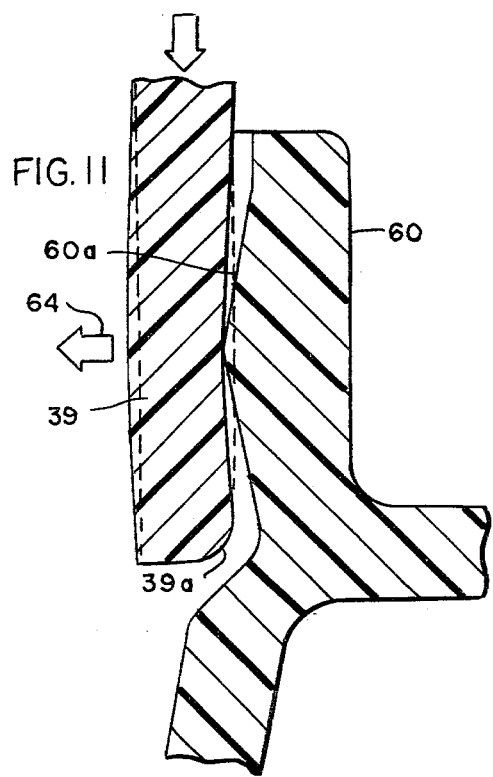
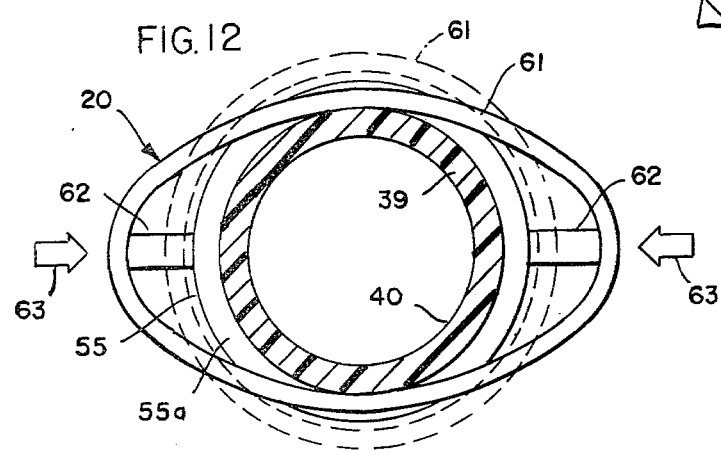

VALVED DRAIN ASSEMBLY FOR UROSTOMY POUCH

BACKGROUND AND SUMMARY

A urostomy pouch or bag of the type exemplified by co-owned U.S. Pat. Nos. 3,523,534 and 3,822,704 is capable of being worn continuously by a patient for several days or more before being removed and replaced by a fresh pouch. During the period of continuous wear, such a pouch must be periodically drained of its fluid contents by manipulating a drain valve at the pouch's lower end. While periodic draining is a necessary and acceptable inconvenience during hours while the wearer is awake, it is an objectionable inconvenience during hours of rest.

Drainage pouches are currently available which are designed to be coupled to drainage tubes leading to relatively large volume bedside containers, thereby permitting exudate to drain continuously through the pouches into the containers so that the user's sleep need not be interrupted by the necessity of periodically emptying the contents of the pouches. While sound in principle, such arrangements have not been entirely successful in practice because of a variety of problems, including difficulties in manipulating the valves and couplings, and tendencies to wear rapidly and leak in use, or to obstruct flow and cause distension and possible rupture of the pouches. There is also the risk that excessive force applied during manipulation of a valve, or in coupling or uncoupling a drainage tube, may impose undue strain on the walls of the drainage pouch, resulting in tearing of the pouch and leakage of its contents. Such risks may be increased if the fittings of the pouch are blocked from direct view by the user, or where the user suffers from some condition or disease, such as arthritis, which makes manipulation of the valve and coupling more difficult.

More specifically, current drainage pouches are sometimes equipped with soft plastic drainage nozzles equipped with removable caps of the same material. When a drainage tube is to be connected, the cap is simply removed, a separate connector is attached to the nozzle, and the tube of the drainage set is then coupled to the connector. Although such a nozzle construction has the advantages of softness and flexibility, thereby reducing the possibilities of pouch rupture, manipulative difficulties exist and are increased by the need for an additional part (connector). Also, experience indicates that such constructions are more prone to leakage over periods of extended use.

In another type of commercially-available construction, the drainage pouch is equipped with a sleeve valve designed to be operated by sliding one telescoping part with respect to another part. While such a valve is advantageous in terms of ease of operation, the act of coupling the valve to a drainage tube is more difficult. Also, because such a construction involves the provision of relatively small flow passages through the valve, such passages have a tendency to be clogged by the more viscous components (e.g., mucus) of the exudate. Where such problems are likely to arise, users are instructed to disassemble the valves prior to attachment of the drainage tubes, such disassembly thereby increasing the complexities and likelihood of user problems, including loss of parts, in performing the manipulative steps.

Accordingly, it is an object of the present invention to provide a drain assembly for a urostomy pouch which overcomes the defects and disadvantages of prior drain assemblies. Specifically, it is an object to provide a drain valve which is easily operated even when out of the user's line of sight, is highly effective in blocking the flow of fluid when adjusted into a closed position, even after periods of extended use, cannot be manipulated to produce inadvertent disassembly of the valve elements, is not likely to obstruct flow (because the passages through the valve are of a cross section at least as large as the drainage tube), and is constructed so that even if excessive force and/or improper technique are used to manipulate the valve, the possibilities of failure of the assembly or damage to the drainage pouch to which the assembly is connected are non-existent or at least extremely remote.

A further object is to provide a drain assembly which includes a drainage tube equipped with a coupler which may be easily and effectively operated to attach the tube to the hollow stem of the valve and to disconnect the tube from that stem. Despite the ease with which the coupler may be operated to latch or unlatch it from the stem, such coupler forms a highly effective leak-resistant seal with the stem and coacts with the stem to produce a secure latch capable of resisting disengagement by all forces exerted on the drainage tube that might be expected to develop during use of the assembly. In addition to greater effectiveness of operation, the coupler, as it is slipped into latching position, coacts with the valve stem to produce an audible snap or click to assure the user that the parts are latched securely together.

Briefly, the drain assembly comprises a body member adapted to be mounted within a urostomy pouch at the lower end thereof, a tubular valve member rotatably connected to the body member, and a drainage tube equipped at one end with a coupler for releasably engaging the tubular stem of the valve member. The body member has walls defining a generally cylindrical discharge chamber, such chamber having a side opening and a lower end opening. The valve member includes a sleeve portion which is rotatably received within the chamber of the body member through the lower end thereof, such valve member also having an open-ended tubular stem which projects downwardly below the body member. The sleeve portion of the valve member has a lateral port which is registrable with the side opening of the body member when the valve member is rotated into an open position, such lateral port being out-of-register with such side opening when the valve member is rotated into a closed position. Locking means secures the body and valve members against axial displacement without at the same time preventing relative rotation of the parts.

Each of the body and valve members is formed of a semi-rigid plastic material, the plastic of the valve member being more rigid (or less flexible) than that of the body member. An integral bead is formed about the lateral port of the valve member and forceably engages the more yieldable material of the body member to produce a highly effective primary or internal seal. A secondary or external seal is formed between an annular flange at the lower end of the body member and the more rigid material of the valve member, such contact occurring within an annular upwardly-facing channel formed in the valve member about the sleeve portion thereof.

The body member also includes a pair of diametrically-disposed lateral extensions, such extensions having side surfaces which extend along converging planes and which terminate in lateral edges substantially parallel with the axis of the body member. In addition, the body member includes a top wall which merges with such lateral edges to form corners, and a pair of thin flexible stress-relieving tabs which are formed integrally with the body member and which project radially and upwardly from such corners.

The tubular stem of the valve member is provided with an annular shoulder spaced above the stem's open lower end, such shoulder having an upwardly-facing latching surface and a downwardly and inwardly inclined camming surface. The coupling means of the drainage tube takes the form of a flexible tubular connector which is secured to the drainage tube and dimensioned to sealingly receive the lower portion of the valve stem. Such coupling means also includes latching means in the form of a flexible oval latching ring extending along a plane normal to the axis of the tubular connector and joined thereto by a pair of flexible arms. Normally the flexible ring assumes an oval configuration in which its minimum inside diameter approximates the outside diameter of the stem and is less than the greater diameter of the latching shoulder; however, when finger pressure is applied to opposite ends of the oval latching ring, such ring may be temporarily reformed or distorted into a generally circular configuration in which its inside diameter exceeds the diameter of the shoulder, thereby permitting the coupler to be removed from the stem of the valve member.

Other advantages, objects, and features of the invention will become apparent from the specification and drawings.

DRAWINGS

FIG. 1 is a fragmentary side elevational view of a complete assembly embodying the invention, the coupler of the drainage tube being shown disconnected from the stem of the valve assembly for clarity of illustration.

FIG. 2 is an exploded perspective view of the major components.

FIG. 3 is a perspective view illustrating the body member and valve member in separated condition.

FIG. 4 is a top plan view of the valve assembly.

FIG. 5 is a longitudinal sectional view taken along line 5—5 of FIG. 4 and showing the valve assembly in closed condition.

FIG. 6 is a longitudinal sectional view similar to FIG. 5 but showing the valve assembly in open condition.

FIG. 7 is an enlarged fragmentary sectional view showing the relationship between the valve member and body member.

FIG. 8 is a greatly enlarged fragmentary sectional view illustrating the line contact which is responsible for the primary seal between the parts.

FIG. 9 is an enlarged fragmentary sectional view depicting the relationship which produces the secondary seal.

FIG. 10 is a side elevational view illustrating the relationship between the valve member and coupling member in longitudinal section.

FIG. 11 is a greatly enlarged fragmentary sectional view showing the formation of the seal between the coupler and the valve stem.

FIG. 12 is an enlarged cross sectional view taken along line 12—12 of FIG. 10.

DETAILED DESCRIPTION

Referring to the drawings (FIGS. 1 and 2), the numeral 10 generally designates an ostomy pouch or bag having front and rear walls 11 and 12 formed of flexible fluid-impermeable thermoplastic sheet material. The front wall 11 and rear wall 12 are sealed around their peripheries by a heat-sealed bond 13 or by any other suitable means. The flexible walls may be formed of any effective gas and liquid impervious thermoplastic material such as, for example, a polyolefin film laminated with an appropriate barrier material. A particularly suitable commercial material comprises low density polyethylene coextruded with a coextensive layer or core of polyvinylidene chloride. Such material is commercially available under the designation "Saranex" from Dow Chemical Company, Midland, Mich.

The rear panel of the ostomy pouch, in accordance with standard practice, is provided with a stoma-receiving opening surrounded by a patch coated with a conventional pressure-sensitive medical adhesive. Neither the opening nor the patch are depicted in the drawings since they would be located near the upper end of the pouch; however, such elements are well known and are disclosed, for example, in co-owned U.S. Pat. Nos. 3,804,091, 3,759,260, 3,822,704, and 3,523,534. Details of the stoma-receiving opening, the adhesive attachment patch, the gasket which may be used to form an effective seal about the stoma, and the attachment means which may take the form of a belt, are all shown and described in such patents, the disclosures of which are incorporated by reference herein.

The drain assembly is generally designated by the numeral 15 and comprises a body member 16, a valve member 17, and a drainage tube assembly 18. The drainage tube assembly includes a standard flexible drainage tube 19 formed of polyvinyl chloride or other suitable material and a coupler 20. The coupler is adapted to make sealing engagement with the stem of the valve member 17 in the manner hereinafter described, such parts being shown in separated condition in FIG. 1 for clarity of illustration. It is to be understood that during waking hours the wearer of the ostomy appliance would normally maintain the parts uncoupled with the valve member in closed condition and that the parts would ordinarily be coupled, with the valve member in open condition (shown in dashed lines in FIG. 1), when the user is at rest, or is bedridden or otherwise incapacitated. Under the latter conditions, the opposite end of the flexible drainage tube would be connected to, or inserted into, a suitable bedside receptacle 21 positioned on the floor or in any case at a level sufficiently below the user to insure proper gravity flow.

The body member 16 and valve member 17 together constitute a valve assembly for controlling drainage from pouch 11. The body member includes a generally cylindrical wall 22 defining a cylindrical discharge chamber 23 having a side opening 24 and a lower end opening 25, all as shown most clearly in FIG. 3. The member also includes a top wall 26 having a central aperture 27.

A pair of extensions 28 and 29 project laterally from the cylindrical core of the body member, such extensions being diametrically disposed with one extension 28 having a greater radial dimension than the other extension 29. Extension 28 is defined by side walls 28a, bottom wall 28b, and top wall 28c (FIGS. 2 and 3). The side walls extend outwardly along converging planes, terminating in a lateral edge 30 which extends vertically, that is, in a direction parallel with the axis of the cylindrical chamber 23. The bottom and side walls 28b and 28a, along with an interior wall 28d, combine to define a cavity 31 which is disposed adjacent to and communicates directly with chamber 23 through lateral opening 24. As illustrated in FIGS. 2–5, the top wall (or upper end wall) 28c has an aperture 32 which exposes cavity 31. To increase the rigidity and strength of the part, the body member may also include a partition or septum 33 which divides cavity 31, but it is to be understood that such partition may be omitted where the reinforcing action is deemed unnecessary.

Like extension 28, extension 29 includes a pair of converging side walls 29a and a top wall 29c. The side walls 29a project outwardly and converge along a lateral edge 34 which is parallel with edge 30 and with the central axis of cylindrical chamber 23. Lateral edges 34 and 30 may be slightly rounded in section so that they do not constitute cutting edges. Similarly, the side and top surfaces of the body member intersect along edges which are smoothly rounded so that they do not constitute sharpened edges capable of cutting the thermoplastic film of the drainage pouch 11.

At the upper corners of the body where lateral edges 30 and 34 merge with top walls 28c and 29c, respectively, are a pair of flexible planar tabs 35, such tabs projecting radially and upwardly from the corners and being coplanar with the lateral edges and with each other. As depicted, the tabs are laterally elongated and smoothly curved in outline; that is, they have no corners which might tend to pierce or cut into the film of the pouch. Since the entire body member is molded from a semi-rigid but flexible or yieldable plastic material such as, for example, medium or low density polyethylene, tabs 35 will flex and thereby function as strain relievers to protect the material of the pouch from damaging contact with the upper corners of the body member and the lateral edges of that member.

The valve member 17 is similarly molded of a semi-rigid plastic material although such material should be more rigid, or less flexible and yieldable, than the material of body member 16. High density polyethylene has been found particularly effective as the fabricating material for the valve member, but other polymeric materials such a polypropylene might be used.

The valve member 17 includes a tubular sleeve portion 36 which is rotatably received within the chamber 23 of the body member. Referring in particular to FIG. 3, it will be seen that the tubular sleeve portion is provided with a lateral port which, upon rotation of the valve member, may be moved into and out of register with side opening 24 of the body member. When the valve member is rotated into its closed position, a smoothly-rounded bead 38 which extends about port 37 forceably engages the flexible wall defining the cylindrical chamber 23 to form a primary seal between the parts. FIGS. 7 and 8 reveal that such contact between the more rigid material of valve member 17 and the more flexible material of the body member 22 results in a slight but perceptable deformation of the body member, thereby producing tight contact that insures an effective seal.

The valve member also includes a tubular stem portion 39 which is coaxial with sleeve portion 36 and which projects downwardly therefrom as a continuation or extension of the sleeve. The stem is open at its lower end and defines a generally cylindrical flow passage 40. When the valve member is rotated into its open position (FIG. 6), the lateral port 37 of the sleeve is in direct register with the side opening 24 of the body member and communicates with the upwardly-opening cavity 31 of that member. Liquid may therefore flow from the interior of the ostomy pouch into the open topped cavity 31 and then into flow passage 40 through aligned openings 24 and 37. It is significant that the area of port 37 approximates, and is at least as large, as the cross sectional area of flow passage 40 and, hence, is at least as large as the internal cross sectional area of flexible drainage tube 19. Since the side opening 24 of the body member, and also the top opening 32 of that member, each has an area greater than the area of lateral port 37, the valve assembly imposes no appreciable restriction on the drainage of fluid from the pouch or bag 10. Furthermore, because of the relatively large size of such openings and port, the possibilities of the drain assembly becoming clogged by mucus or other viscous constituents of the exudate are remote.

Referring to FIGS. 7 and 9, the cylindrical wall 22 of the body member includes a depending annular flange 41 having a downwardly and inwardly sloping inner surface 41a. Valve member 17 has an integral annular wall 42 spaced outwardly from the sleeve portion 36 to define an upwardly-facing annular channel 43 which slidably and sealingly receives the depending flange 41 of the body member. In an untensioned or unstressed state (i.e., prior to assembly of the parts), flange 41 has a thickness or width at its lower end which is slightly greater than the width of channel 43. Therefore, when the parts are assembled, the depending flange 41 which, like the remainder of the body member 16 is formed of a polymeric material more resilient than the material of valve member 17, is compressed or deformed slightly to produce tight sealing engagement in the zone of contact x indicated in FIG. 9. Such contact between the normally sloping inner surface 41a at the lower end of flange 41 and the outside surface of sleeve portion 36 produces a secondary seal which is largely responsible for preventing external leakage from the valve assembly. The previously described primary seal, while also protecting against external leakage, performs a major function in preventing internal leakage, that is, in insuring the competency of the valve in its closed position.

The tubular sleeve 36 of the valve member 17 also has a top or upper end wall 44, such end wall having an upstanding integral fastener 45 slotted to provide a pair of flexible hook portions 45a which engage a ledge 46 within top opening 27 of the body member to lock the body and valve members against axial displacement without at the same time preventing relative rotation of such parts (FIG. 7). The resistance to axial separation far exceeds the force which a user might apply to the drain assembly in the manipulation of the valve or of the drain tube assembly 18; consequently, there is virtually no danger that in use the two members of the valve assembly might become separated and cause accidental release of the contents of the pouch.

The valve member is provided with diametrically-disposed lateral extensions or wings which correspond generally to the lateral extensions 28 and 29 of the body member. Extension 47 projects radially outwardly a distance greater than extension 48. The two extensions 47, 48 are coplanar with their common plane extending through the axis of the valve body. As shown in FIG. 5, the lateral dimension of extension 48 approximates the corresponding dimension of extension 28; similarly, the lateral dimension of extension 48 generally matches the corresponding dimension of extension 29. Therefore, a user can readily determine by touch and without visual inspection when the valve member 17 is in its closed position. In that condition, the valve assembly assumes its most compact configuration with the lateral extensions of the respective members being in register as shown.

The valve assembly is open by rotating valve member 17 180° into the offset position depicted in FIG. 6. Since the extensions of the valve member are then out of register with the corresponding extensions of the valve body, a user may again readily determine by sense of touch that the valve member 17 is in its fully open position.

Stop elememts are provided by the respective members 16 and 17 to assist a user in positioning the valve member 17 in either its fully opened or fully closed position. As revealed in FIGS. 3, 5, and 6, the extensions 47 and 48 of the valve member have upstanding stop elements 49 and 50 respectively, whereas the body member 16 has a single depending stop element 51. When the valve member is closed, stops 49 and 51 engage each other as indicated in FIG. 5, whereas when the valve is fully opened such engagement occurs between stops 50 and 51 (FIG. 6).

The valve assembly is secured to the lower end of the drainage pouch 11 as shown in FIG. 1, with body member 16 disposed between walls 11 and 12 at the extreme lower end of the pouch and with valve member 17 projecting downwardly below the pouch. While various means might be utilized to secure the body member to the walls of the pouch so that the pouch's fluid contents may escape only through the passages of the valve assembly, a particularly effective manner of attachment is believed to consist of heat sealing lower edge portions of the pouch's walls directly to the side surfaces of the thermoplastic body member 16 as a continuation of the same heat seal zones 13 which join the walls of the pouch to each other.

The tubular stem 39 of the valve member 17 is provided with an annular shoulder 55 spaced above the stem's lower end and below lateral extensions 47 and 48. The configuration of the shoulder is clearly revealed in FIG. 7 where it will be seen that the shoulder has an upwardly facing latching surface 55a which extends in a plane normal to the axis of the stem and a downwardly and inwardly inclined camming surface 55b. Such shoulder cooperates with the coupler 20 of the drainage tube assembly for detachably securing the parts together in the manner described below.

The coupler 20 is formed integrally of a tough flexible plastic material having substantial elastic memory. While any of a variety of materials might be used, particularly effective results have been obtained when the coupler is fabricated of an acetal resin marketed under the designation Delrin by E. I. duPont deNemours, Wilmington, Del. The coupler includes a tubular connector 60, a latching ring 61, and a pair of arms or straps 62 which join the connector and latching ring together. As clearly illustrated in FIGS. 1, 2, 10, and 12, the latching ring 61 is coaxial with the tubular connector 60 and is non-circular or oval in configuration. When the flexible spring-like latching ring 61 is in a normal or untensioned state, its minimum inside diameter (i.e., its inside diameter measured across the shorter axis) approximates the outside diameter of stem 39 and is less than the outside diameter of shoulder 55 (FIG. 12). Therefore, with the parts in the assembled condition indicated in FIGS. 10 and 12, the latching ring 61 is restrained by the upwardly-facing latching surface 55a of the shoulder from being separated or pulled from the stem. However, if finger pressure is applied in the direction of arrows 63 in FIG. 12, the oval latching ring may be easily reformed into a generally circular configuration (represented by dashed lines) in which the ring will have a generally uniform inside diameter greater than latching shoulder 55. Therefore, by simply squeezing the ring into a generally circular configuration, a user may easily detach the coupler from stem 39.

Ideally, the flexible arms or straps 62 join the oval latching ring 61 at the zones of sharpest curvature of that ring. Such locations facilitate operation of the coupler since the user may readily locate the arms by touch and, simply by squeezing such arms towards each other as shown in FIG. 10, may reform the ring into a generally circular unlatching condition.

The tubular connector 60 is dimensioned to receive the lower portion of the stem 39, specifically, the portion of the stem below latching shoulder 55. The interior of the tubular connector includes a reduced portion 60a which has an inside diameter slightly smaller than the outside diameter of the stem when the connector is in an untensioned or unstressed state. When the parts are urged together, the sloping surface of the connector's reduced portion 60a engages the rounded surface 39a at the lower end of the stem to cam or flex the wall of the stem inwardly in the direction of arrow 64, as shown in some exaggerated form in FIG. 11. A fluid tight seal is therefore produced between the inner surface of the connector 60 and the outer surface of stem 39. Such seal is not limited to a precise location along the length of the stem (it is formed when the stem first reaches the zone of smallest diameter of the connector's inside surface 60a and remains in effect as the parts are further telescoped together), nor does it require any particular rotational orientation of the connector with respect to the stem.

As the coupling is advanced upwardly towards its fully latched position, the latching ring 61 engages the sloping undersurface 55b of the shoulder 55 to force opposite side portions of the ring outwardly until the ring clears the shoulder. The moment the ring passes the shoulder, its opposite side portions snap back into the position shown in solid lines in FIG. 12 with an audible clicking or snapping sound that informs the user that the parts are fully latched together.

The tapered lower end portion 60b of the connector (FIG. 10) may be permanently secured to the flexible drainage tube 19 by any suitable means. Heat sealing, solvent bonding, or mechanical engagement, or combinations thereof, may be utilized. Where a mechanical frictional interengagement is relied upon, the outer surface of portion 60b may be provided with annular ridges or projections to prevent accidental separation of the drainage tube from the connector.

While in the foregoing an embodiment of the invention has been disclosed in considerable detail for purposes of illustration, it will be understood by those skilled in the art that many of these details may be varied without departing from the spirit and scope of the invention.

I claim:

1. A drain assembly for a urostomy pouch comprising a body member having walls defining a generally cylindrical discharge chamber having a side opening and an end opening; said body member being adapted to be mounted within a urostomy pouch with said side opening communicating with the interior of such pouch and said end opening directed externally thereof; a passage-providing tubular valve member having a generally cylindrical sleeve portion coaxial with said chamber and rotatably received within said chamber through said end opening for rotation about the common axis of said sleeve portion and chamber; said sleeve portion having an open-ended tubular stem projecting beyond said body member; said sleeve portion having a lateral port registrable with said side opening of said body member when said valve member is rotated into an open position and being out-of-register with said side opening when said valve member is rotated into a closed position; said sleeve portion also having an end wall closing the passage of said valve member at the end of said sleeve portion remote from said stem; locking means securing said body and valve members against axial displacement; and a drainage tube equipped at one end with coupling means for releasably engaging said stem.

2. The assembly of claim 1 in which stop means are provided for limiting the extent of rotation of said valve member into said open and closed positions.

3. The assembly of claim 1 in which said port has an area approximating the internal cross sectional area of said drainage tube.

4. The assembly of claim 3 in which said side opening of said body member is larger than said port.

5. The assembly of claim 1 in which said body member includes a pair of diametrically disposed extensions projecting laterally therefrom; each said extension having side surfaces extending along converging planes and terminating in lateral edges substantially parallel with said common axis of said cylindrical chamber and sleeve.

6. The assembly of claim 5 in which said body member also includes an end wall facing in a direction away from said valve member and merging with lateral edges to form corners; and a pair of thin flexible tabs formed integrally with said body member and projecting radially and axially from said corners; said tabs being coplanar with said lateral edges and with each other and being smoothly curved in outline; whereby said flexible tabs may yieldably engage the wall of a urostomy pouch to relieve strain on such wall when a twisting force is applied to said assembly.

7. The assembly of claim 5 in which one of said extensions has a lateral dimension measured from the axis of said cylindrical chamber substantially greater than that of the other of said extensions.

8. The assembly of claim 7 in which said valve member is provided with a pair of diametrically disposed extensions projecting laterally from said stem; said extensions of said valve member being disposed below said extensions of said body member and having lateral dimensions corresponding generally with the lateral dimensions of the extensions of said body member.

9. The assembly of claim 5 in which said one extension of said body member is provided with a cavity communicating directly with said lateral opening; said end wall of said body member having an aperture communicating directly with said cavity; whereby, fluid in a urostomy pouch may pass directly into said cavity through said aperture and then enter said passage of said valve member when the valve member is in its open position.

10. A drain assembly for a urostomy pouch comprising a body member having walls defining a generally cylindrical discharge chamber having a side opening and an end opening; said body member being mounted within a urostomy pouch with said side opening communicating with the interior of such pouch and said end opening directed externally thereof; a passage-providing tubular valve member having a generally cylindrical sleeve portion coaxially and rotatably received within said discharge chamber through said end opening and having an open-ended tubular stem projecting beyond said body member; said sleeve portion having a lateral port registrable with said side opening of said body member when said valve member is rotated into an open position and being out-of-register with said side opening when said valve member is rotated into a closed position; said sleeve portion also having an end wall closing the passage of said valve member at the end of said sleeve portion remote from said stem; locking means securing said body and valve members against axial displacement; and a drainage tube equipped at one end with coupling means for releasably engaging said stem, each of said body and valve members being formed of a semi-rigid plastic material; said plastic material of said valve member having greater rigidity than that of said body member.

11. The assembly of claim 10 in which said valve member has an integral bead extending about said port and sealingly engaging said body member within said chamber.

12. The assembly of claim 11 in which the walls of said body member defining said chamber include a cylindrical wall; said cylindrical wall being flexed outwardly to a limited extent in response to forceful sealing engagement by said bead.

13. The assembly of claim 10 in which said walls of said body member include a cylindrical wall terminating adjacent its free end in an annular flange; said valve member having an integral annular wall spaced outwardly from said sleeve portion to define an annular channel slidably and sealingly receiving said flange.

14. The assembly of claim 13 in which said flange has an inside surface which tapers inwardly towards the free end of said cylindrical wall; said flange when in an unstressed state having a maximum wall thickness which is greater than the width of said channel; whereby, said flange is compressed by reason of forceful sealing engagement with said sleeve portion and said annular wall when said members are fully assembled.

15. A drain assembly for a urostomy pouch comprising a body member having walls defining a generally cylindrical discharge chamber having a side opening and an end opening; said body member being mounted within a urostomy pouch with said side opening communicating with the interior of such pouch and said end opening directed externally thereof; a passage-providing tubular valve member having a generally cylindrical sleeve portion co axially and rotatably received within said discharge chamber through said end opening and having an open-ended tubular stem projecting beyond said body member; said sleeve portion having a lateral port registrable with said side opening of said body member when said valve member is rotated into an open position and being out-of-register with said side opening when said valve member is rotated into a closed position; said sleeve portion also having an end wall closing the passage of said valve member at the end of said sleeve portion remote from said stem; locking means securing said body and valve members against axial displacement; and a drainage tube equipped at one end with coupling means for releasably engaging said stem, said stem having an external annular shoulder located intermediate the length thereof; said shoulder having a latching surface normal to the axis of said stem and facing towards said body member, and a camming surface sloping towards said stem and facing away from said body member; said coupling means comprising a flexible tubular connector secured to said drainage tube and dimensioned to sealingly and releasably receive a portion of said stem; said coupling means also being provided with latching means engagable with said shoulder for latching said stem and connector together.

16. The assembly of claim 15 in which said latching means provided by said coupling means comprises a flexible latching ring extending along a plane normal to the axis of said tubular connector and spaced axially therefrom; and a pair of flexible arms attaching said ring to said connector; said ring in an untensioned state having a minimum inside diameter approximating the outside diameter of said stem and less than the maximum diameter of said shoulder; said ring being capable of being flexed to assume a generally circular outline having an inside diameter greater than the maximum diameter of said shoulder.

17. The assembly of claim 16 in which said ring, arms, and tubular connector are formed integrally of flexible plastic material.

18. The assembly of claim 17 in which said arms are diametrically disposed and join said oval ring adjacent opposing portions of sharpest curvature of said ring.

19. The assembly of claims 15 or 16 in which said tubular connector is provided with an inner surface having an intermediate portion of a diameter smaller than the outside diameter of said stem when said stem and connector are separated and unstressed.

20. The assembly of claim 19 in which said intermediate portion of said inner surface has inwardly-sloping surface portions leading thereto and disposed axially on opposite sides thereof.

21. The assembly of claims 1, 5, 8, 9, 10, 11, 15, or 16 in which a urostomy pouch is provided; said pouch having side walls sealed to said body member so that said side opening of said body member communicates with the interior of said pouch and said end opening of said body member is directed externally of said pouch.

22. A valve assembly for a drainage pouch comprising a body member having walls defining a generally cylindrical discharge chamber having a side opening and an end opening; a passage-providing tubular valve member having a generally cylindrical sleeve portion coaxial with said chamber and rotatably received within said chamber through said end opening for rotation about the common axis of said sleeve portion and chamber; said sleeve portion having an open-ended tubular stem projecting beyond said body member; said sleeve portion having a lateral port registrable with said side opening of said body member when said valve member is rotated into an open position and being out-of-register with said side opening when said valve member is rotated into a closed position; said sleeve portion also having an end wall closing the passage of said valve member at the end of said sleeve portion remote from said stem; and locking means securing said body and valve members against axial displacement without preventing relative rotation of said members.

23. The assembly of claim 22 in which stop means are provided for limiting the extent of rotation of said valve member into said open and closed positions.

24. The assembly of claim 22 in which said port has an area approximating the internal cross sectional area of the passage of said valve member.

25. The assembly of claim 24 in which said side opening of said body member is larger than said port.

26. The assembly of claim 22 in which said body member includes a pair of diametrically disposed extensions projecting laterally therefrom; each said extension having side surfaces extending along converging planes and terminating in lateral edges substantially parallel with said common axis of said cylindrical chamber and said sleeve.

27. The assembly of claim 26 in which said body member also includes an end wall facing in a direction away from said valve member and merging with said lateral edges to form corners; and a pair of thin flexible tabs formed integrally with said body member and projecting radially and axially from said corners; said tabs being coplanar with said lateral edges and with each other and being smoothly curved in outline.

28. The assembly of claim 26 in which one of said extensions has a lateral dimension measured from the axis of said cylindrical chamber substantially greater than that of the other of said extensions.

29. The assembly of claim 28 in which said one extension of said body member is provided with a cavity communicating directly with said lateral opening; said end wall of said body member having an aperture communicating directly with said cavity.

30. The assembly of claim 28 in which said valve member includes a pair of diametrically disposed extensions projecting laterally from said stem; said extensions of said valve member being disposed beneath said extensions of said body member and having lateral dimensions generally corresponding to the lateral dimensions of said extensions of said body member.

31. The assembly of claim 22 in which a ostomy pouch is provided; said pouch having a pair of side walls defining a chamber therebetween; said body member being disposed within said pouch with said side opening communicating with the interior of the pouch and said end opening directed externally thereof; said valve member being oriented with the stem thereof disposed externally of said pouch.

32. A valve assembly for a drainage pouch comprising a body member having walls defining a generally cylindrical discharge chamber having a side opening and an end opening; a passage-providing tubular valve member having a sleeve portion rotatably received within said chamber through said end opening and having an open-ended tubular stem projecting beyond said body member; said sleeve portion having a lateral port registrable with said side opening of said body member when said valve member is rotated into an open position and being out-of-register with said side opening when said valve member is rotated into a closed position; said sleeve portion also having an end wall closing the passage of said valve member at the end of said sleeve portion remote from said stem; and locking means securing said body and valve members against axial displacement without preventing relative rotation of said members, each of said body and valve members being formed of a semi-rigid flexible plastic material; said plastic material of said valve member having greater rigidity than that of said body member.

33. The assembly of claim 32 in which said valve member has an integral bead extending about said port and sealingly engaging said body member within said chamber.

34. The assembly of claim 33 in which the walls of said body member defining said chamber include a cylindrical wall; said cylindrical wall being flexed outwardly to a limited extent in response to forceful sealingly engagement by said bead.

35. The assembly of claim 33 in which said walls of said body member include a cylindrical wall terminating adjacent its free end in an annular flange; said valve member having an integral annular wall spaced outwardly from said sleeve portion to define an annular channel slidably and sealingly receiving said flange.

36. The assembly of claim 35 in which said flange has an inside surface which tapers inwardly towards the free end of said cylindrical wall; said flange when in an unstressed state having a wall thickness adjacent said free end which is greater than the width of said annular channel whereby, said flange is stressed by reason of compressive sealing engagement with said sleeve portion and said annular wall within said channel when said members are fully assembled.

37. A drainage tube assembly adapted to be coupled to a tubular drain stem of a drainage pouch, such stem having an annular latching shoulder disposed intermediate the length of such stem, said assembly comprising a flexible drainage tube provided at one end thereof with a coupler; said coupler including a flexible tubular connector secured to said tube, a flexible oval latching ring coaxial with said connector and spaced axially therefrom, and a pair of flexible arms joining said ring and connector; said ring in an unflexed state having a minimum inside diameter approximating the outside diameter of a drain stem and less than the maximum diameter of a latching shoulder extending about such stem; said ring being capable of assuming a generally circular configuration when a squeezing force is applied thereto.

38. The assembly of claim 37 in which said connector, ring, and arms are formed integrally of flexible plastic material.

39. The assembly of claim 37 in which said arms are diametrically disposed and join said oval ring along portions of sharpest curvature thereof.

40. The assembly of claim 37 in which said tubular connector is provided with an inner surface having a portion of reduced diameter.

41. The assembly of claim 40 in which said inner surface portion of reduced diameter is disposed intermediate the length of said connector and has inwardly-sloping frusto-conical inner surface portions leading thereto and disposed axially on opposite sides thereof.

* * * * *